United States Patent [19]

Wirthlin

[11] Patent Number: 5,796,472
[45] Date of Patent: Aug. 18, 1998

[54] OPTICAL TRANSLUCENCY INDICATOR FOR MEASUREMENT OF AIR FILTER DIRTINESS, LIQUID LEVEL, THICKNESS, AND OTHER PARAMETERS

[76] Inventor: Alvin R. Wirthlin, 3101 Jeanlin Dr., SE., Grand Rapids, Mich. 49546

[21] Appl. No.: 802,453

[22] Filed: Feb. 18, 1997

Related U.S. Application Data

[60] Provisional application No. 60/025,647 Aug. 10, 1996.
[51] Int. Cl.$^6$ .............. G01N 21/00; G01B 9/10; G02B 6/00
[52] U.S. Cl. .......... 356/72; 356/436; 356/438; 250/227.14; 250/227.18; 250/227.31; 385/12
[58] Field of Search .............. 356/436–440; 250/227.14, 227.18, 227.31; 385/12, 14, 13

[56] References Cited

U.S. PATENT DOCUMENTS

| | | | |
|---|---|---|---|
| 3,658,421 | 4/1972 | Shelton | 356/72 |
| 4,371,897 | 2/1983 | Kramer | 250/227.31 |
| 4,747,364 | 5/1988 | Horowitz . | |
| 4,880,990 | 11/1989 | Rando | 250/577 |
| 4,934,183 | 6/1990 | Sommer et al. | 356/438 |
| 5,070,237 | 12/1991 | Okuyama et al. | 250/227.31 |
| 5,132,530 | 7/1992 | Groh et al. | 250/227.31 |
| 5,141,309 | 8/1992 | Wörwag | 356/72 |
| 5,315,672 | 5/1994 | Padovani | 250/227.11 |

FOREIGN PATENT DOCUMENTS

| | | |
|---|---|---|
| 0186138 | 7/1986 | European Pat. Off. . |
| 60-117116 | 6/1985 | Japan . |
| 60-164286 | 8/1985 | Japan . |
| 2-170084 | 6/1990 | Japan . |
| 2-184706 | 7/1990 | Japan . |
| 2 173 894 | 10/1986 | United Kingdom . |

*Primary Examiner*—Frank G. Font
*Assistant Examiner*—Jason D. Vierra-Eisenberg
*Attorney, Agent, or Firm*—Alvin R. Wirthlin

[57] ABSTRACT

An optical detector for determining the degree of translucency of a medium includes an elongate collector that gathers radiant energy along its length and transmits the gathered energy to its ends. A sensor is positioned in proximity to at least one of the collector ends to detect the amount of radiant energy received by the collector. The amount of radiant energy received by the collector and transmitted to the sensor is proportional to the degree of average translucency of the medium. In one embodiment, the medium is a filter and the degree of detected translucency is directly proportional to the degree of filter contamination. In another embodiment, the medium is a liquid and the degree of detected translucency is directly proportional to liquid level. The collector is preferably formed from one or more fluorescent-doped fiber optics. When a plurality of fiber optics is used, the ends thereof may be terminated in one or more sleeves such that radiant energy transmitted along their lengths can be detected by the sensor.

22 Claims, 5 Drawing Sheets

Fig. 11

OPTICAL TRANSLUCENCY INDICATOR FOR MEASUREMENT OF AIR FILTER DIRTINESS, LIQUID LEVEL, THICKNESS, AND OTHER PARAMETERS

This application claims the benefit of U.S. Provisional application Ser. No. 60/025,647 filed on Sep. 10, 1996.

BACKGROUND OF THE INVENTION

1. Field of the Invention

This invention relates to translucency measurement of an object or medium, and more particularly to the measurement of change in translucency from a first state to a second state of the object or medium, such as the translucency of a filter from a clean state to a dirty state or the measurement of liquid level from a first level to a second level.

2. Description of the Related Art

The performance of internal combustion engines, heating and air conditioning systems, air purifiers, and many other system requiring an air filter depends at least in part on the cleanliness of the filter. In motor vehicles, a typical air filter is made of a cellulose fiber material that is pleated to create a large filter area over a relatively small intake opening. The fiber material is usually either sandwiched between or bordered by one or more dust seals and a wire mesh is located on each side of the material to provide compressive strength and flame resistance in case of backfire.

No matter what device the air filter is associated with, air normally passes through the filter with relatively low restriction when the filter is new. Over time, however, dust and other particles present in the air can build up on the outer surface and clog the filter pores. When the filter is clogged, the device may operate inefficiently due to restricted air flow through the filter.

The use of differential air pressure for detecting the dirtiness of automotive air filters is well known. As air flow is reduced through the filter, the differential pressure between inner and outer walls of the filter increases. However, the filter dust seals may be weak, distorted, or improperly seated, and therefore allow the entrance of unfiltered air, especially when the filter is clogged, to thereby reduce the differential air pressure and give a false reading. Moreover, the differential air pressure in some systems may vary with varying air flow through the filter, such as in turbocharger systems, air purifiers, vacuums, heating and air conditioning systems, etc., and therefore falsely indicate that the filter needs replacement. Pressure transducers for measuring differential air pressure can also be cost prohibitive.

It is a common practice in the automotive repair industry to remove the filter from the vehicle and place an illuminated light bulb between the filter and an observer to determine if the filter needs replacement. If no light can be seen through the filter, the filter is typically replaced. However, this technique is left largely to personal judgement and therefore produces inconsistent results from one observer to another. In addition, it is very difficult to determine the most efficient time to change the filter since it is usually checked only during routine maintenance intervals.

U.S. Pat. No. 5,141,309 to Worag discloses an optical detector for indicating the dirtiness of an air filter. The detector includes a light emitter and receiver that are oriented to detect either the amount of light passing through a filter material or the amount of light reflected therefrom. This detector only measures the dirtiness of an air filter at a single point. In order to obtain an average dirtiness indication, a plurality of detectors must be placed at different locations along the filter surface and circuitry must be provided to calculate an average reading from the plurality of detector readings. Detection of the dirtiness of an air filter at a single point is inconclusive of the air filter condition due to uneven air flow across the filter in many systems. Uneven air flow causes dirt or other contaminates to collect unevenly over the surface area or volume of the filter. Although the provision of a plurality of detectors and averaging circuitry gives a better indication of filter dirtiness, the added cost of these components is often prohibitive.

Another difficulty associated with prior art detectors lies in the field of liquid level detectors for motor vehicles, such as fuel level detectors. The prior art detectors usually include a float that rides on a surface of the gasoline in a fuel tank. The float is connected to a pivot arm that causes a change in an electrical circuit when the float and arm move. When a vehicle accelerates or travels up an incline, turns, or decelerates or descends an incline, the upper surface of the fuel is at an acute or complex angle with respect to a bottom of the tank. The float and arm move along with the upper surface of the fuel and thus give a false reading of the actual fuel level in the tank.

SUMMARY OF THE INVENTION

These and other problems of the prior art are overcome by the provision of an apparatus for measuring the translucency of a medium. According to one aspect of the invention, an apparatus for detecting the degree of translucency of a medium includes an emitter for projecting radiant energy at least partially through a medium and a collector spaced from the emitter for receiving the projected radiant energy. In one embodiment, the medium is an air filter and the degree of detected translucency is directly proportional to filter contamination. In another embodiment, the medium may include a liquid and/or gas and the degree of detected translucency is directly proportional to liquid level in a liquid holding tank.

Preferably, the collector has opposite ends and is formed such that radiant energy from the emitter can be gathered along its length and transmitted to its ends. A suitable collector may comprise one or more fluorescent-doped fiber optics.

The medium can be constantly or intermittently monitored to detect any change in translucency. The term "translucent" and its derivatives as used herein refers to any state from and including completely transparent to and including completely opaque. In addition, the term "medium" as used herein refers to one or more layers of solid or fluid material, including liquid and gas.

According to a further aspect of the invention, a system for detecting the degree of contamination of an air filter that is disposed in an air flow path for filtering contaminants from the air, includes an emitter for emitting radiant energy and a collector spaced from the emitter and adapted to be disposed in the air flow path. The collector has opposite ends and is formed such that radiant energy from the emitter can be gathered along its length and transmitted to its ends. A sensor is provided in proximity to at least one of the collector ends for detecting the amount of radiant energy transmitted to the at least one collector end from the emitter. The amount of radiant energy received by the collector and transmitted to the sensor is proportional to the degree of contamination of the air filter. Preferably, the collector comprises one or more fluorescent-doped fiber optics. In one embodiment, the collector is positioned in proximity to and/or within the air filter. In a further embodiment, the collector is located remotely from the air filter, such as at the air intake of an air filter housing.

According to an even further aspect of the invention, a method for determining the translucency of a medium includes providing an elongate collector in a flow path of the medium, the collector having opposite ends and being formed such that radiant energy can be gathered along its length and transmitted to its ends. Radiant energy is emitted toward the collector and the amount of radiant energy received by the collector is detected. The translucency of the medium is then determined, which is reflective of the amount of detected radiation. In one embodiment, the translucency of the medium is reflective of the degree of air filter contamination. In another embodiment, the translucency of the medium is reflective of liquid level.

BRIEF DESCRIPTION OF THE DRAWINGS

The invention will now be described with reference to the drawings in which.

DETAILED DESCRIPTION OF THE PREFERRED EMBODIMENTS

Referring now to the drawings, and to FIGS. 1 and 2 in particular, a filter contamination detector 10 is illustrated in connection with an air filter 14 (shown in dashed line). The detector 10 includes a light collector 18 and a light sensor 24 positioned at the ends 22 of the collector 18. A porous backing sheet 20 may be provided for supporting the collector 18.

The collector 18 is elongate and is preferably formed such that radiant energy can be gathered along its length and transmitted to its ends. A suitable collector 18 can be constructed of an elongate fluorescent fiber optic or scintillating fiber optic and may be secured to the porous backing sheet 20 through adhesives, clamps, or other well known fastening means. The backing sheet 20 is preferably constructed of a permeable material, such as plastic or metal mesh, woven cloth, etc., so as to allow the free flow of air therethrough. Instead of the backing sheet 20, the fiber optic 18 may be contained in a clear tube (not shown) or embedded in clear plastics material to adequately support and protect the fiber optic, especially when subject to a harsh environment. In some applications, the backing sheet 20 may be eliminated and the fiber optic can be placed in proximity to or in direct contact with the filter.

A suitable fluorescent fiber optic may be constructed of a polystyrene-based core containing one or more fluorescent dopants that is surrounded by a polymethyl methacrylate (PMMA) cladding. When such a fiber receives radiation along its length, energy is absorbed in the fiber at a certain wavelength and is re-emitted at both ends of the fiber at a higher energy and longer wavelength. Thus, depending on the amount of radiation absorbed by the fiber along its length, a proportionate amount of radiation is emitted at the fiber ends 22.

A light source 16 is positioned in proximity to the collector 18 and the filter 14 and may be a fluorescent light or any other source that emits radiant energy in the visible light spectrum. Alternatively, the light source may be of the infra-red or ultra-violet type. The light sensor 24 may be a photocell, phototransistor or other light-sensitive element, and is arranged at the collector ends 22 so as to detect only light emanating therefrom. When an infra-red light source is used, the sensor 24 is of the infra-red type, such as an infrared phototransistor.

Figure 1:
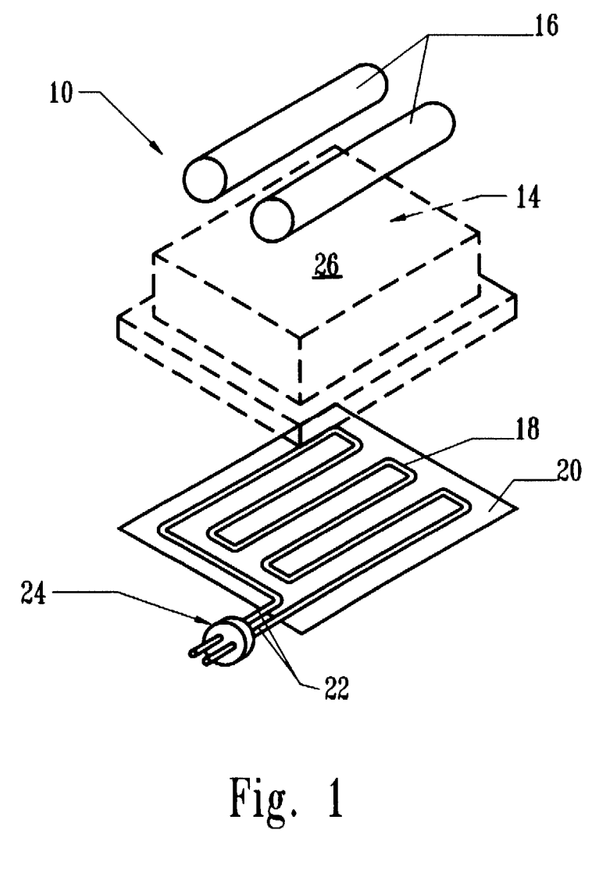
FIG. 1 is a perspective view of an air filter contamination detection system according to the invention, with a light collector positioned below an air filter.
Figure 2:
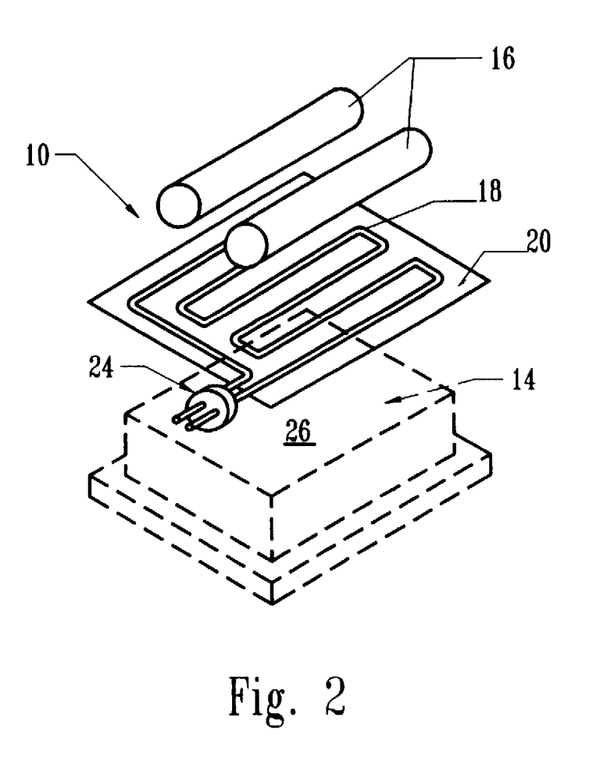
FIG. 2 is a perspective view similar to FIG. 1 with the light collector positioned above the filter.

The collector 18 as shown in FIGS. 1 and 2 has a tortuous shape that extends over a length and width of the filter 14, so as to cover representative areas of the entire air filter such that an average degree of filter contamination can be measured by the sensor 24. In some air filtration systems, some sections of the filter may be subject to a greater amount of dust or other particulate deposits than other sections, due at least in part to uneven air flow across the filter. Thus, the light incident on the fiber optic 18 and measured by the sensor 24 is a reflection of the average degree of filter contamination and thus the overall resistance of air flow through the filter.

In FIG. 1, the filter 14 is positioned between the light source 16 and the fiber optic 18. In this manner, the fiber optic 18 is protected from dust, particles and other contaminants. The light source 16 may also be suitably shielded or sealed from the environment.

In FIG. 2, the fiber optic 18 is positioned between the light source and the filter and is therefore directly exposed to the dust, particles and other contaminants present in the environment. The fiber optic 18 is placed in the airflow path of the filter 14, such that contaminants present on the fiber optic 18 are reflective of contaminants on the face 26 of the filter 14. It is preferred that the fiber optic 18 be arranged transverse to the direction of air flow in order to expose the greatest surface area of the fiber optic to the air flow. However, the fiber optic may alternatively be arranged parallel to the air flow or at any angle with respect thereto. As contaminants build up on the fiber optic 18 and filter 14, the amount of light absorbed by the fiber optic diminishes and is therefore indicative of the filter condition. In this manner, the filter detector 10 can be supported by the filter itself or other support structure associated with the filter with little or no modification to the filter or support structure. The collector 18 and light source 16 may be located remotely from the filter, such as at the air intake of an air filter housing, as long as the collector 18 is positioned in the airflow path of the filter.

Figure 3:
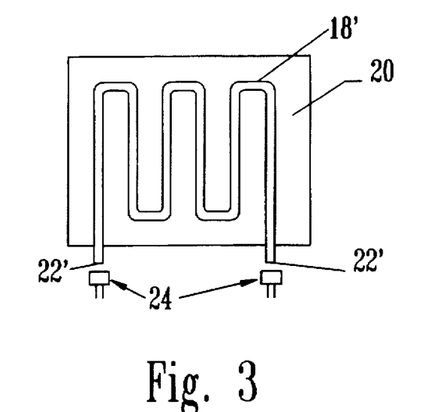
FIG. 3 is a top plan view of the light collector according to a second embodiment of the invention.

With reference now to FIG. 3, a collector 18' in the form of a fluorescent fiber optic according to a second embodiment of the invention is shown, wherein like parts in the previous embodiment are represented by like numerals. The collector 18' is similar to the embodiment in FIGS. 1 and 2 with the exception that the ends 22' of the collector 18' are spaced apart. A sensor 24 is positioned at each end 22' for detecting radiation emanating therefrom.

Figure 4:
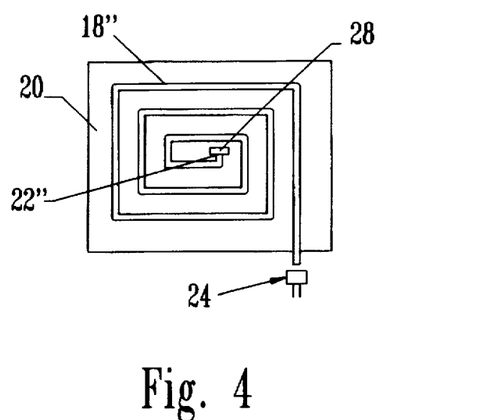
FIG. 4 is a top plan view of the light collector according to a third embodiment of the invention.

Referring now to FIG. 4, a collector 18" in the form of a fluorescent fiber optic according to a third embodiment of the invention is shown, wherein like parts in the previous embodiments are represented by like numerals. The collector 18" is arranged in a spiral shape on the backing sheet 20. A mirror 28 is positioned at one end 22" of the fiber optic so as to redirect light emanating therefrom back through the fiber optic to the opposite end 22". A sensor 24 is positioned for detecting radiation emanating from the opposite end 22". Alternatively, the mirror 28 may be eliminated or replaced with a second detector 24.

Figure 5:
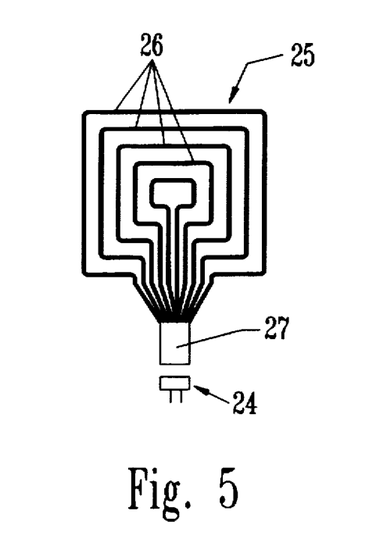
FIG. 5 is a top plan view of the light collector according to a fourth embodiment of the invention.

With reference now to FIG. 5, an array 25 of fluorescent fiber optics 26 are arranged in a predetermined pattern such that there is no overlap of fibers in the light collecting area of the filter. The ends of the fibers 26 are terminated in a sleeve 27 through well known techniques and a light sensor 24 is placed adjacent to the sleeve 27 for sensing light from the plurality of fibers 26. The use of fluorescent fibers having different dopants for collecting and emitting light in different frequencies is contemplated. Instead of terminating both ends of each fiber in the sleeve 27, only one end of each fiber may be terminated in the sleeve, with a free end of each fiber extending across the flow path of the filter. The free end of each fiber may be connected to a surface of the filter, a filter housing, or may be embedded in the filter itself. Alternatively, the fiber free ends may be terminated in a second sleeve and a second sensor may be provided in proximity thereto.

Figure 5A:
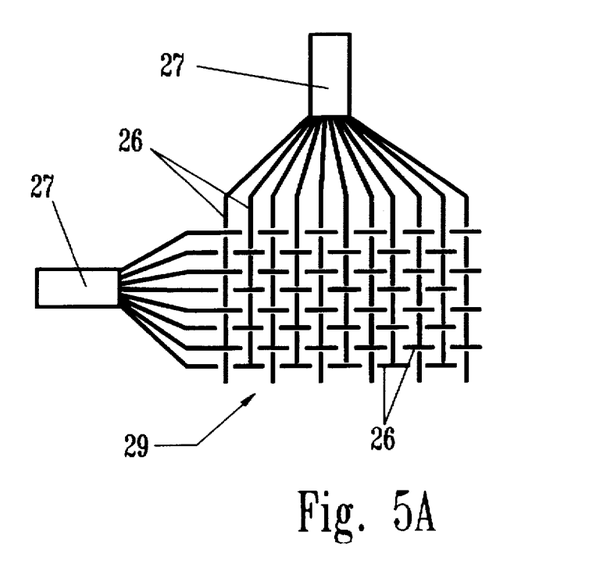
FIG. 5A is a top plan view of the light collector according to a fifth embodiment of the invention.

In an alternative arrangement, the fluorescent fibers 26 can be woven together to form a light collector sheet 29 with the ends of the fibers contained in one or more sleeves 27, as illustrated in FIG. 5A. When the light collector sheet 29 is used to detect the dirtiness of an air filter, there should be a sufficient amount of voids in the sheet and the voids should be of a sufficient size so as to unimpede the flow of air through the sheet.

Figure 6:
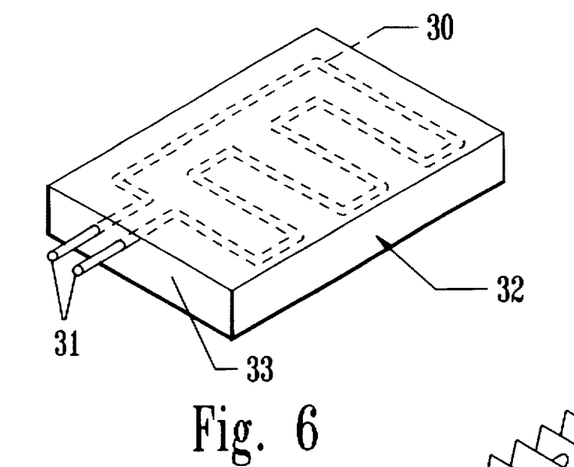
FIG. 6 is a perspective view of the light collector embedded in an air filter.
Figure 7:
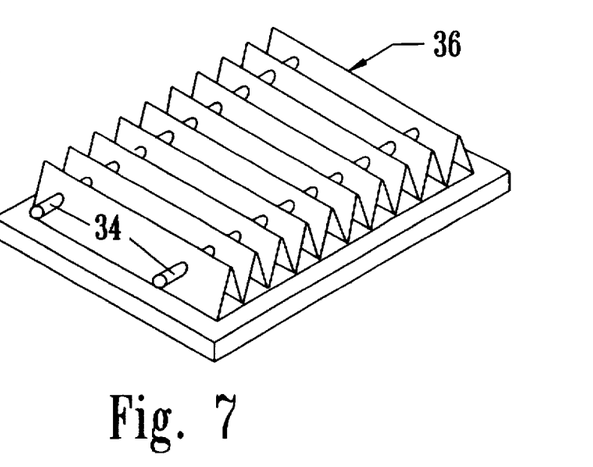
FIG. 7 is a perspective view of the light collector partially embedded in a pleated air filter.
Figure 8:
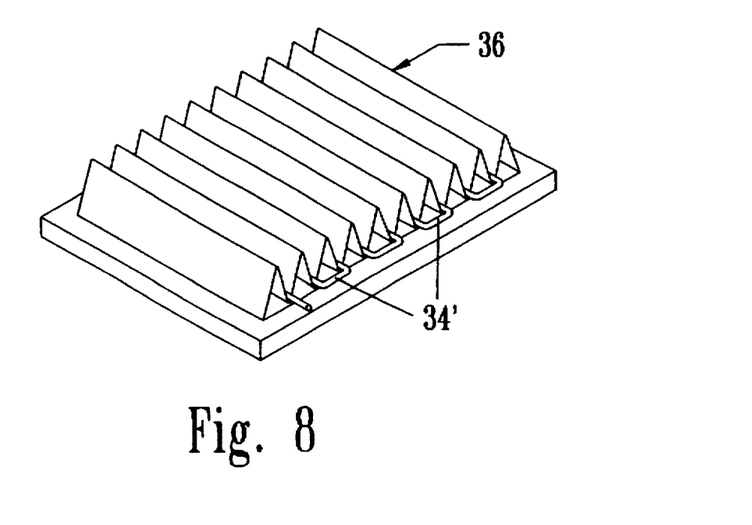
FIG. 8 is a perspective view of the light collector positioned on an outer surface of a pleated air filter.

Although the previous embodiments show the collector 18 placed either above or below the filter, a collector in the form of a fluorescent fiber optic 30 (shown in dashed line) can be placed within a filter 32 during manufacture so as to be completely encapsulated therein, as shown in FIG. 6. Alternatively, a fluorescent fiber optic 34 can be stitched into a pleated filter 36 (FIG. 7), such that part of the fiber optic is embedded in the filter and part is exposed to the environment.

The fluorescent fiber optics described in the previous embodiments can be of the scintillating type and are preferably round in cross section in order to give the greatest amount of light transfer efficiency as compared to fiber optics having square or triangular cross sections. Fiber optics of this type commonly range in diameter from about 0.25 mm to about 5 mm.

Figure 9:
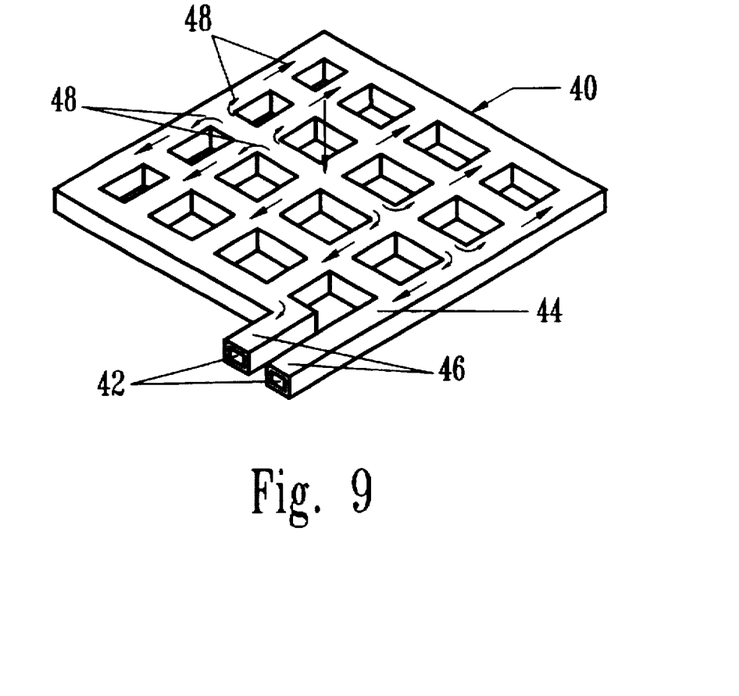
FIG. 9 is a perspective view of a light collector according to a further embodiment of the invention.

With reference now to FIG. 9, a light collector 40 according to a further embodiment of the invention includes a fluorescent doped core material 42 that is square in cross section and arranged in a mesh pattern. A cladding 44 completely surrounds the core material 42 except at the end 46. The core material is preferably molded in a single operation after which the cladding is applied through well known techniques, such as vacuum deposition. With this arrangement, light is absorbed into the core material and directed along pathways as represented by arrows 48. Any light emitted from the end 46 is proportional to the light absorbed by the core material 42. A sensor (not shown) can be arranged proximal to the ends 46 to detect light emitted therefrom.

Figure 10:
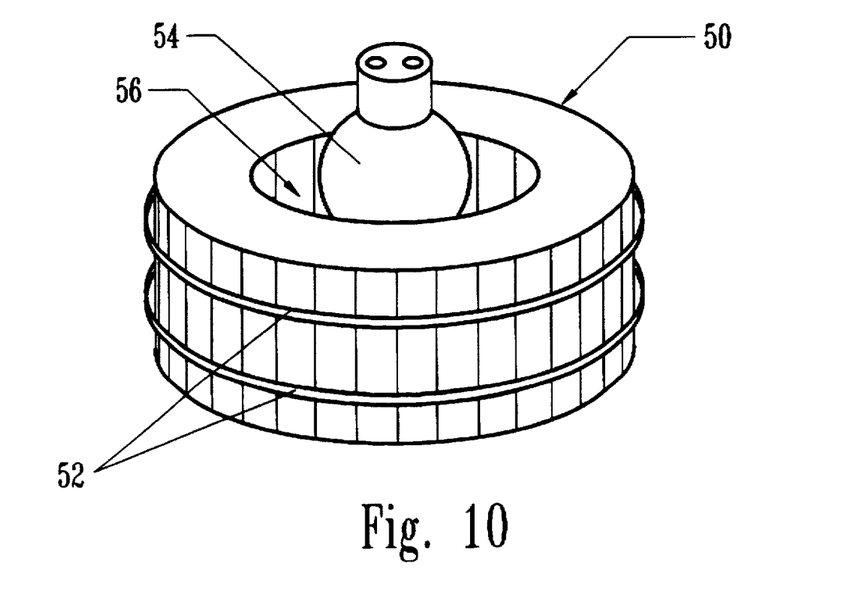
FIG. 10 is a perspective view of a pleated cylindrical air filter element and detector assembly according to a further embodiment of the invention.

With reference now to FIG. 10, a cylindrical pleated air filter 50 has a light collector in the form of a pair of fluorescent fiber optics 52 wrapped around an outer periphery thereof. A non-explosive light source 54 is positioned in a central opening 56 of the filter 50 to illuminate the filter. A portion of any light passing through the filter is absorbed by the fiber optics 52 and detected by one or more sensors 24. Although two fiber optics are shown, more or less can be provided depending on the height of the filter and the desired accuracy in determining filter contamination. Alternatively, a single fiber optic can spiral around the filter and therefore take the place of two or more fibers that wrap around the filter a single time. As in the previous embodiments, the position of the fiber(s) and light source can be reversed. The fibers may alternatively be at least partially embedded in the filter material. When the light source is positioned outside of the filter, a curved fluorescent light, LED array, electroluminescent strip or other elongate light source may be used to provide a substantially uniform light around the outer periphery of the filter.

In all of the previous embodiments, the light source and detector may be operated constantly or intermittently. Well known circuitry (not shown) can be connected to the detector 24 to provide an indication of the filter condition. Such circuitry may drive a single indicator LED when the dirtiness of the filter passes a predetermined set point to give an indication that the filter needs replacement, or may drive an array of LED's when the filter passes sequential predetermined set points to give an indication as to how much useful filter life is left. Alternatively, the circuitry may drive a digital display or other well known display device to give more precise indication of the degree of filter contamination or the amount of remaining filter life.

The above-described embodiments can be dimensioned for a particular filter size. It is also contemplated however, that a universal frame can be provided, wherein the sides and/or ends of the frame can expand or contract to accompany a wide variety of filter sizes. The frames may be adjusted by way of telescopic frame members and one or more fluorescent-doped fiber optics can extend between frame members. The fiber optics should be formed extra long to accommodate expansion of the frame.

Although the detector embodiments set forth above have been described in conjunction with sensing the dirtiness of an air filter, it is to be understood that the detector can be used in other environments, such as sensing the dirtiness or thickness of liquids, curtains, rugs, carpets, etc., or non-contact sensing of paper thickness over discrete areas during manufacture, etc.

Figure 11:
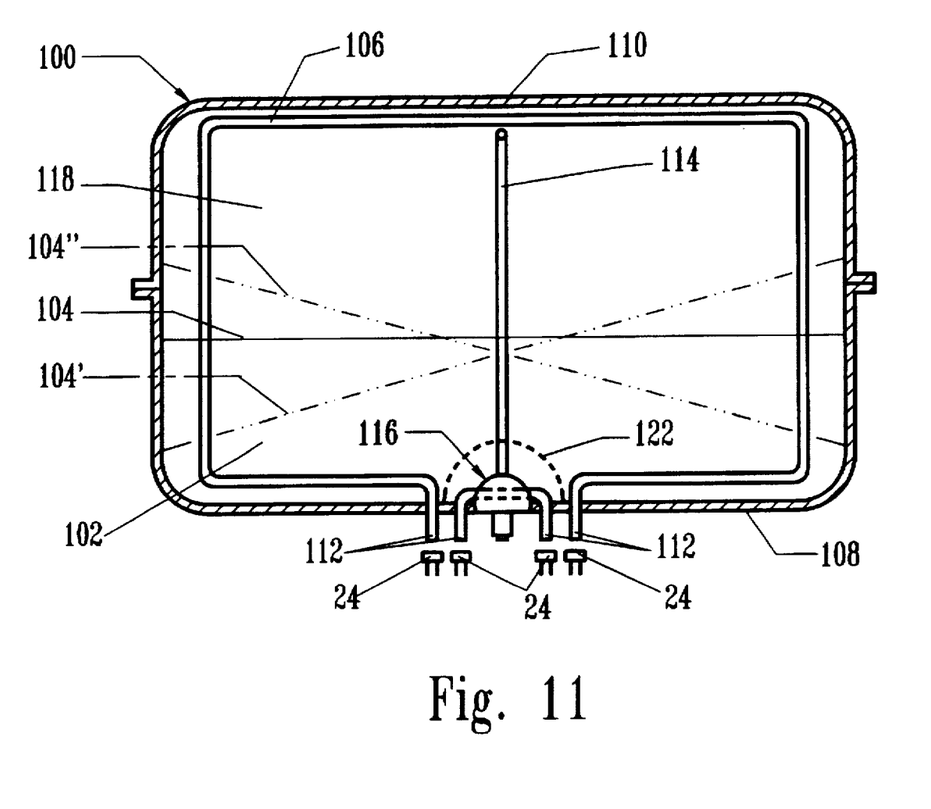
FIG. 11 is a side elevational view of a liquid holding tank with an optical level detection system according a further embodiment of the invention.

With reference now to FIG. 11, another application of the fluorescent fiber optic and light combination is illustrated. A tank 100 includes a liquid 102, such as gasoline, that is initially level, as shown by line 104. A first collector in the form of a first generally inverted U-shaped fluorescent fiber optic 106 extends from a bottom 108 of the tank 100 to a top 110 thereof and returns to the bottom of the tank. Each end 112 of the fiber optic 106 extends downwardly from the tank bottom 108 and is proximal to a light detector 24. A second collector in the form of a second generally inverted U-shaped fiber optic 114 is similar in shape to the first fiber optic and extends transverse thereto. Each end (not shown) of the second fiber optic 114 is also proximal to a light detector 24. A non-explosive light 116 is positioned centrally between the fiber optics 106 and 114. The transmission of light through the liquid 102 is different than the transmission of light through the air 118. This difference can be accurately detected by how much light emitted from the light source is absorbed by the fiber optic collectors, which is reflective of actual fuel level. The collectors are preferably located in the flow path of fuel in the tank, such that when the fuel moves, equal portions of the collector are simultaneously covered and uncovered by the fuel. A unique advantage of this arrangement over prior art detectors is particularly evident when a vehicle carrying the tank 100 accelerates or travels up an incline such that the fuel upper surface 104' is at an acute angle with respect to the bottom 108 and top 110 of the tank 100. Likewise, when decelerating or descending an incline, the fuel upper surface fuel upper surface 104" is at an acute angle with the bottom an The incline can become complex when ascending or descending inclines or accelerating or decelerating while experiencing centrifugal acceleration, such as when the vehicle is turning. The prior art liquid level detectors that depend on the upper surface of the liquid are inaccurate under these circumstances. With the present invention, however, the amount of light transmitted through the fuel 102 and the air 118 in the tank 100 and received by the collectors remains essentially unchanged during acceleration or gravitational forces. Thus, fuel level reading is not changed by movement of the fuel in the tank due to acceleration. However, as the tank is filled or emptied, the amount of collector surface area covered by the liquid varies to change the amount of light absorbed by the collectors to thereby give accurate fuel level readings.

A third fluorescent optical fiber 120 may be spaced a small distance from the light source 116 and extends at least partially therearound. The ends of the optical fiber 120 are connected to a pair of light detectors 24 to detect the translucency of the fuel, since fuel clarity may differ from one filling station to another or from one grade of fuel to another. Well known comparator circuitry can be provided to take fuel translucency into account when measuring fuel level with the fiber optics 106, 114. The fiber optics may be coated with a transparent material, such as a polymer, that is resistant to gasoline, oils, etc.

Although a single light source at the bottom of the tank is shown, it is to be understood that one or more light sources may be provided at the top or sides of the tank as an alternative to or in addition to the light source at the bottom of the tank. Instead of forming a collector with a generally U-shaped single fluorescent fiber optic, a plurality of fiber optics may alternatively be terminated in a sleeve at one end for transmitting collected light to a single sensor 24 outside of the tank, while their free ends are attached to an upper inner surface of the tank. The average amount of light present on the fibers will remain unchanged during movement of liquid in the tank caused by acceleration forces.

While particular embodiments of the invention have been shown, it will be understood that the invention is not limited thereto since modifications may be made by those skilled in the art, particularly in light of the foregoing teachings. Reasonable variation and modification are possible within the foregoing disclosure of the invention without departing from the scope of the invention.

The embodiments for which an exclusive property or privilege is claimed are defined as follows:

1. An apparatus for detecting the degree of translucency of a medium, the apparatus comprising:
    an elongate collector adapted for placement at least in proximity to the medium to extend across a predefined area of the medium, the collector having opposite ends and being formed such that radiant energy can be gathered along its length and transmitted to its ends;
    an emitter spaced from the collector and positioned to project radiant energy at least partially through the medium within the predefined area and onto the collector; and
    a sensor positioned in proximity to at least one of the collector ends for detecting the amount of radiant energy transmitted to the at least one collector end;
    wherein the amount of radiant energy received by the collector within said predefined area and transmitted to the sensor is proportional to the degree of translucency of the medium.

2. An apparatus according to claim 1, wherein the emitter emits light in one of the visible, infra-red and ultra-violet spectrums, and the collector collects light in the one spectrum.

3. An apparatus according to claim 1, wherein the collector comprises at least one fluorescent-doped fiber optic.

4. An apparatus according to claim 1, wherein the collector comprises a plurality of fluorescent-doped fiber optics.

5. An apparatus according to claim 4, wherein the at least one collector end comprises at least one end of each of the plurality of fiber optics terminated in a sleeve.

6. An apparatus according to claim 4, wherein the plurality of fiber optics are woven together to form a fiber optic collector sheet.

7. An apparatus according to claim 1, and further in combination with a medium, and wherein at least a portion of the medium is located between the emitter and the collector.

8. An apparatus according to claim 7, wherein the medium comprises a filter and wherein the degree of detected translucency is directly proportional to the degree of filter contamination.

9. An apparatus according to claim 7, wherein the medium comprises a liquid and the degree of detected translucency is directly proportional to liquid level.

10. A system for detecting the degree of contamination of an air filter that is disposed in an air flow path for filtering contaminants from the air, the system comprising:
    an elongate collector adapted for disposal in the air flow path for receiving radiant energy, the collector having opposite ends and being formed such that radiant energy can be gathered along its length and transmitted to its ends;
    an emitter for projecting radiant energy at least through a portion of the filter and onto the collector; and
    a sensor positioned adjacent at least one of the collector ends for detecting the amount of radiant energy transmitted to the at least one of the collector ends from the emitter;
    wherein the amount of radiant energy received by the collector and transmitted to the sensor is proportional to the degree of contamination of the air filter.

11. A system according to claim 10, wherein the collector comprises at least one fluorescent-doped fiber optic.

12. A system according to claim 10, wherein the collector is located at a remote position from the air filter.

13. A system according to claim 10, wherein the air filter is positioned between the emitter and the collector.

14. A system according to claim 10, wherein at least a portion of the collector is disposed in the air filter.

15. A system according to claim 10, and further comprising:
   a circuit for receiving and processing signals from said sensor; and
   a display operatively associated with said circuit for indicating the degree of contamination of the filter.

16. A method for detecting the translucency of a medium, comprising:
   providing an elongate collector in a flow path of the medium, the collector having opposite ends and being formed such that radiant energy can be gathered along its length and transmitted to its ends;
   emitting radiant energy toward the collector and at least through a portion of the medium;
   detecting the amount of emitted radiant energy received by the collector; and
   determining the translucency of the medium based on the detected amount of radiant energy received by the collector.

17. A method according to claim 16, wherein the step of providing a collector includes providing at least one fluorescent-doped fiber optic.

18. A method according to claim 17, wherein the step of providing at least one fluorescent-doped fiber optic includes providing a plurality of fluorescent-doped fiber optics.

19. A method according to claim 16, wherein the medium comprises a liquid, and the medium flow path is movement of the liquid, and wherein the step of determining the translucency of the medium includes determining a level of the liquid.

20. A method according to claim 16, wherein the medium comprises a filter and the medium flow path is an air flow path through the filter, and wherein the step of determining the translucency of the medium includes determining the degree of filter contamination.

21. A system for detecting the degree of contamination of an air filter for filtering contaminants from the air, the system comprising:
   an air filter having a body constructed of material that is permeable to air; and
   an elongate collector connected to the air filter and extending over a predefined area of the air filter body, the collector having opposite ends and being formed such that radiant energy from a radiation source can be gathered along its length and transmitted to its ends;
   wherein the amount of radiant energy received by the collector within the predefined area and transmitted to the collector ends is proportional to the degree of contamination of the air filter.

22. A system according to claim 21, wherein the collector comprises at least one fluorescent-doped fiber optic.

* * * * *